United States Patent [19]

Dusza et al.

[11] 4,447,442

[45] May 8, 1984

[54] 3-TRIFLUOROACETYLAMINO-1-ARYL-2-PYRAZOLINES

[75] Inventors: John P. Dusza, Nanuet, N.Y.; Joseph P. Joseph, Montvale, N.J.; Seymour Berstein, New City, N.Y.

[73] Assignee: American Cyanamid Company, Stamford, Conn.

[21] Appl. No.: 406,603

[22] Filed: Aug. 9, 1982

Related U.S. Application Data

[63] Continuation-in-part of Ser. No. 282,972, Jul. 13, 1981, Pat. No. 4,348,527.

[51] Int. Cl.$^3$ .................... A01N 43/56; A61K 31/415
[52] U.S. Cl. ............................... 424/273 P; 548/362
[58] Field of Search ................... 424/273 P; 548/362

[56] References Cited

FOREIGN PATENT DOCUMENTS

22578 1/1981 European Pat. Off. ............ 548/362

OTHER PUBLICATIONS

Radmark et al., Febs. Letters 1980, vol. 110(2), pp. 213–215.
Nijkamp et al., Eur. J. Pharmacol. 1980, vol. 62, pp. 121–122.

*Primary Examiner*—Richard Raymond
*Attorney, Agent, or Firm*—Anne M. Rosenblum

[57] ABSTRACT

This disclosure describes novel 3-substituted amino-1-phenyl-2-pyrazolines and 3-substituted amino-1-mono and disubstituted phenyl-2-pyrazolines and their $C_4$ and $C_5$ analogs, useful for meliorating the inflammation and/or the progressive joint deterioration characteristic of arthritic disease, preventing the onset of asthmatic symptoms and allergic diseases, or as analgesic, antibacterial or antifungal agents.

52 Claims, No Drawings

3-TRIFLUOROACETYLAMINO-1-ARYL-2-PYRAZOLINES

CROSS REFERENCE TO RELATED APPLICATION

This application is a continuation-in-part of our co-pending application, Ser. No. 282,972, filed July 13, 1981, now issued as U.S. Pat. No. 4,348,527 with issuance date of Sept. 7, 1982.

PRIOR ART

1. R. Battisti, et. al., U.S. Pat. No. 4,149,005 (Apr. 10, 1979) discloses compounds of the formula:

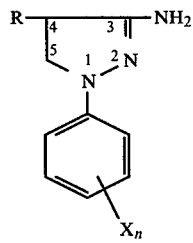

where R is H or $CH_3$, X is H, Br, Cl, alkyl, alkoxy or carboxyalkyl groups with from 1 to 4 carbon atoms or $CF_3$; and n is 1 or 2. These are disclosed as being used as intermediates in the preparation of 1-phenyl-3-aminopyrazoles as coupling components in azo dye manufacture. Related foreign patents: Ger. Offen. No. 2,727,706; French No. 2,355,834; Gr. Br. Pat. No. 1,515,500; Belgium No. 855,944; Netherland No. 7,706,760 and Japan No. 28,168.

2. G. A. Higgs, et. al., (Wellcome Research Laboratories) Biochemical Pharmacology, 28 1959 (1979) discloses 3-amino-1-[m-(trifluoromethyl)phenyl]-2-pyrazoline (BW 755C);

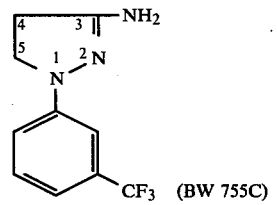

This compound is reported to have anti-inflammatory activity.

BRIEF SUMMARY OF THE INVENTION

This invention relates to new organic compounds and more particularly is concerned with novel 3-substituted amino-1-phenyl-2-pyrazolines and 3-substituted amino-1-mono and disubstituted phenyl-2-pyrazolines and their $C_4$ and $C_5$ analogs which may be represented by the following general formulae:

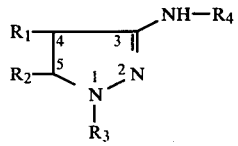

wherein $R_1$ is hydrogen or lower alkyl ($C_1$-$C_4$); $R_2$ is hydrogen, lower alkyl ($C_1$-$C_4$), phenyl or

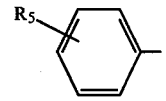

where $R_5$ is halogen; $R_3$ is

where $R_6$ and $R_7$ are the same or different and may be hydrogen, chloro, fluoro, lower alkyl ($C_1$-$C_4$), trifluoromethyl or $COCF_3$; $R_4$ is —CHO, —$COCF_3$ or —$COR_8$ where $R_8$ is lower alkyl ($C_1$-$C_4$) and the pharmacologically acceptable acid-addition salts thereof.

DETAILED DESCRIPTION OF THE INVENTION

The novel compounds of the present invention are generally obtainable as white to pale yellow crystalline solids having characteristic melting points and absorption spectra. The bases are appreciably soluble in solvents such as acetone, ethanol, toluene, methylene chloride and the like but are relatively insoluble in water. The organic bases of the present invention form non-toxic acid-addition salts with a variety of pharmacologically acceptable organic and inorganic salt forming reagents. Thus, acid-addition salts, formed by admixture of the organic free base with one or two equivalents of an acid, suitably in a neutral solvent, are formed with such acids as sulfuric, phosphoric, hydrochloric, hydriodic, sulfamic, citric, lactic, fumaric, succinic, tartaric, acetic, benzoic, gluconic, ascorbic, and the like. The acid-addition salts are relatively insoluble in non-polar organic solvents such as diethyl ether, benzene, toluene, and the like but are appreciably soluble in water. For purposes of this invention, the free bases are equivalent to their non-toxic acid-addition salts.

Preparation of the novel 3-substituted amino-1-heteroaryl-2-pyrazolines IV of the instant invention, which exhibit the pharmaceutical activity as herein described, is accomplished by the adaptation of the procedure of Duffin, G. F. and Kendall, J. D., J. Chem. Soc., 1954, 408; in accordance with the following reaction scheme:

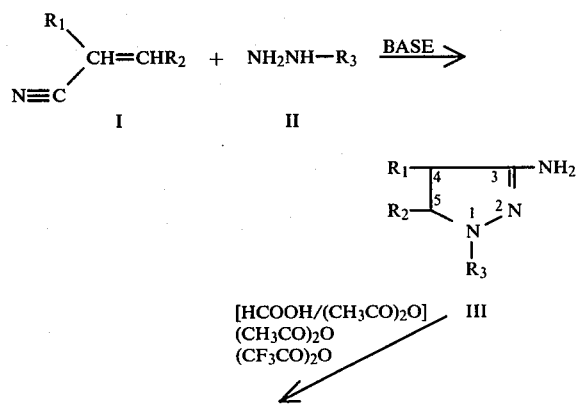

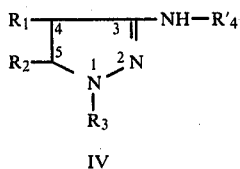

-continued wherein $R_1$, $R_2$, $R_3$ and $R_4$ are as previously defined.

In accordance with the above reaction scheme, an arylhydrazine or a halogen-mono or disubstituted arylhydrazine or salt thereof II such as phenylhydrazine, m-chlorophenylhydrazine hydrochloride, p-chlorophenylhydrazine hydrochloride, m- and p-fluorophenylhydrazine hydrochloride, m-tolylhydrazine hydrochloride, m-trifluoromethylphenylhydrazine hydrochloride and 3,4-dichlorophenylhydrazine hydrochloride is reacted with an $\alpha,\beta$-unsaturated nitrile I, such as acrylonitrile, methacrylonitrile, crotononitrile, cinnamonitrile, p-chlorocinnamonitrile, 4-methylcinnamonitrile, butyl acrylonitrile or a compound such as $\beta$-ethoxypropionitrile (which can undergo base catalyzed elimination to yield I) in a base catalyzed condensation procedure, with a base such as sodium ethoxide or choline hydrate in absolute ethanol. The reaction mixture is refluxed for a period of from 2-20 hours, then the solvent is removed in vacuo. Water addition gives a filterable solid which is collected, dissolved in dichloromethane and passed through a short column of a hydrous magnesium silicate. The effluent is then refluxed with the gradual addition of solvent such as hexane until crystallization is noted.

Recrystallization from the same solvent pair (with or without additional treatment with a hydrous magnesium silicate) or from acetone-hexane provides the 3-amino-1-aryl-2-pyrazoline and 3-amino-1-mono and disubstituted phenyl-2-pyrazoline compounds III. If the pyrazoline III is not soluble in dichloromethane, recrystallization may be accomplished from acetone-hexane, 95% ethanol or benzene with the omission of the hydrous magnesium silicate treatment phase.

The pyrazoline compound III is then subjected to N-acylation by treating with an acylating agent such as a mixture of formic acid and acetic anhydride (Feiser and Feiser, Reagents for Organic Synthesis, Vol. 1, page 4), acetic anhydride or propionic anhydride (with or without a catalyst such as 4-dimethylamino pyridine) or with trifluoroacetic anhydride at room temperature for 2-48 hours to yield the corresponding novel products of the invention IV which for the most part may be recrystallized from dichloromethane-hexane.

The compounds of the instant invention have utility as pharmacological agents. They are active either as anti-inflammatory agents, analgesic agent, antibacterial and/or antifungal agents and in some cases are active in more than one of these areas. Some of the compounds of this invention are further useful in inhibiting the progression of arthritis such as rheumatoid arthritis and inhibiting the progression of joint deterioration or preventing the onset of asthma and other allergic diseases. They also find utility in the amelioration or prevention of pathological reactions such as osteoarthritis, gout, acute synovitis and psoriasis.

Representative compounds of this invention have been proven to be active in vivo as anti-inflammatory agents when tested by the Carrageenin Induced Edema of the Rat Paw Test. This test is a modification of the method of Winter, C. A., et al., Proc. Soc. Exp. Biol. and Med., 111, 544 (1962). Compounds found to be active in this test are:

2,2,2-Trifluoro-N-(4-methyl-1-phenyl-2-pyrazolin-3-yl)-acetamide
N-[1-(3,4-Dichlorophenyl)-3-pyrazolin-3-yl]formamide
N-[1-(p-Chlorophenyl)-5-methyl-2-pyrazolin-3-yl]formamide
N-[1-(p-Fluorophenyl)-5-methyl-2-pyrazolin-3-yl]acetamide
N-(1-Phenyl-2-pyrazolin-3-yl)propionamide
2,2,2-Trifluoro-N-(1-phenyl-2-pyrazolin-3-yl)acetamide
2,2,2-Trifluoro-N-[1-(p-fluorophenyl)-2-pyrazolin-3-yl]-acetamide
N-[1-(p-Fluorophenyl)-5-methyl-2-pyrazolin-3-yl]propionamide Another in vivo method of determining drug effect on conditions which result in the production of pain is measuring the effect on ultraviolet induced erythema in guinea pigs [Winder, C. V., et al., A Study of Pharmacological Influences on Ultraviolet Erythema in Guinea Pigs, Arch. Int. Pharmacodyn., 116, 261 (1958)]. A representative compound of the present invention which is active when tested by the ultraviolet induced erythema test is N-[1-(p-fluorophenyl)-5-methyl-2-pyrazolin-3-yl]acetamide.

A test used to show activity against chronic inflammation in adjuvant arthritis is a modification of the technique of Newbald, B., "Chemotherapy of Arthritis Induced In Rats by Mycobacterial Adjuvant," Brit. J. Pharmacol. Chemother., 21, 127 (1963), which is described in U.S. Patent 3,863,010. Representative compounds of the present invention found to be active when tested by the Adjuvant Arthritis Test are:

N-[1-(p-Chlorophenyl)-5-methyl-2-pyrazolin-3-yl]-2,2,2-trifluoroacetamide
2,2,2-Trifluoro-N-[1-(p-fluorophenyl)-5-methyl-2-pyrazolin-3-yl]acetamide The compounds of the present invention also possess activity as analgesic agents. A method employed for measuring the in vivo activity of the compounds of the present invention is the "writhing syndrome" test for analgesic activity as described by Siegmund, et al., Proceedings of the Society for Experimental Biology and Medicine, 95, 729 (1957), with modifications as described in U.S. Pat. No. 3,863,010. Representative compounds of the present invention which are active when tested by the "writhing syndrome" test are listed as follows:

2,2,2-Trifluoro-N-[5-methyl-1-(p-trifluoroacetylphenyl)-2-pyrazolin-3-yl]acetamide
2,2,2-Trifluoro-N-(4-methyl-1-phenyl-2-pyrazolin-3-yl)-acetamide
N-(1,5-Diphenyl-2-pyrazolin-3-yl)-2,2,2-trifluoroacetamide
N-[1,5-Bis(p-chlorophenyl)-2-pyrazolin-3-yl]-2,2,2-trifluoroacetamide
N-(5-Methyl-1-phenyl-2-pyrazolin-3-yl)acetamide
N-[1-(p-Fluorophenyl)-5-methyl-2-pyrazolin-3-yl]acetamide
N-(1-Phenyl-2-pyrazolin-3-yl)propionamide
N-(1-m-Tolyl-2-pyrazolin-3-yl)acetamide
2,2,2-Trifluoro-N-[4-methyl-1-($\alpha,\alpha,\alpha$-trifluoro-m-tolyl)-2-pyrazolin-3-yl]acetamide
2,2,2-Trifluoro-N-[1-(p-fluorophenyl)-5-phenyl-2-pyrazolin-3-yl]acetamide
2,2,2-Trifluoro-N-[1-(p-fluorophenyl)-5-methyl-2-pyrazolin-3-yl]acetamide N-[1-(p-Fluorophenyl)-5-methyl-2-pyrazolin-3-yl]propionamide
N-[1-(p-Fluorophenyl)-4-methyl-2-pyrazolin-3-yl]formamide
N-[5-(p-Chlorophenyl)-1-(m-fluorophenyl)-2-pyrazolin-3-yl]-formamide Representative compounds of the present invention have been proven active in vitro as antibacterial and/or antifungal agents when tested by such procedures as the standard agar dilution procedure. Compounds proven active in this test include:

N-[1-(3,4-Dihchlorophenyl)-2-pyrazolin-3-yl]-2,2,2-trifluoroacetamide
2,2,2-Trifluoro-N-[5-methyl-1-(p-trifluoroacetylphenyl)-2-pyrazolin-3-yl]acetamide
2,2,2-Trifluoro-N-(4-methyl-1-phenyl-2-pyrazolin-3-yl)-acetamide
2,2,2-Trifluoro-N-(4-methyl-1-(p-trifluoroacetylphenyl)-2-pyrazolin-3-yl]acetamide
N-(1,5-Diphenyl-2-pyrazolin-3-yl)-2,2,2-trifluoroacetamide
N-[1-(m-Chlorophenyl)-2-pyrazolin-3-yl]-2,2,2-trifluoroacetamide
N-[1,5-Bis(p-chlorophenyl)-2-pyrazolin-3-yl]-2,2,2-trifluoroacetamide
N-[1-(3,4-Dichlorophenyl)-5-methyl-2-pyrazolin-3-yl]-2,2,2-trifluoroacetamide
N-[1-(3,4-Dichlorophenyl)-4-methyl-2-pyrazolin-3-yl]formamide
N-[1-(3,4-Dichlorophenyl)-2-pyrazolin-3-yl]formamide
N-(1-Phenyl-2-pyrazolin-3-yl)acetamide
N-[1-(m-Chlorophenyl)-2-pyrazolin-3-yl]formamide
N-[1-(p-Chlorophenyl)-5-methyl-2-pyrazolin-3-yl]formamide
N-[1-(p-Chlorophenyl)-5-methyl-2-pyrazolin-3-yl]-2,2,2-trifluoroacetamide
N-(1-Phenyl-2-pyrazolin-3-yl)formamide
N-[1-(m-Chlorophenyl)-4-methyl-2-pyrazolin-3-yl]formamide
N-(5-Methyl-1-phenyl-2-pyrazolin-3-yl)acetamide
N-[1-(p-Fluorophenyl)-5-methyl-2-pyrazolin-3-yl]acetamide
N-[5-(p-Chlorophenyl)-1-(m-fluorophenyl)-2-pyrazolin-3-yl]-acetamide
N-[5-(p-Chlorophenyl)-1-(p-fluorophenyl)-2-pyrazolin-3-yl]acetamide
N-[1-(p-Chlorophenyl)-4-methyl-2-pyrazoline-3-yl]acetamide
N-(1-Phenyl-2-pyrazolin-3-yl)propionamide
N-[1-(m-Fluorophenyl)-4-methyl-2-pyrazolin-3-yl]acetamide
N-(1-m-Tolyl-2-pyrazolin-3-yl)acetamide
2,2,2-Trifluoro-N-(1-phenyl-2-pyrazolin-3-yl)acetamide
N-(1,5-Diphenyl-2-pyrazolin-3-yl)formamide
2,2,2-Trifluoro-N-[1-(p-fluorophenyl)-2-pyrazolin-3-yl]-acetamide
2,2,2-Trifluoro-N-[1-(4-trifluoroacetyl-m-tolyl)-2-pyrazolin-3-yl]acetamide
2,2,2-Trifluoro-N-[1-(p-fluorophenyl)-5-phenyl-2-pyrazolin-3-yl]acetamide
2,2,2-Trifluoro-N-[1-(p-fluorophenyl)-5-methyl-2-pyrazolin-3-yl]acetamide
N-[1-(p-Fluorophenyl)-5-methyl-2-pyrazolin-3-yl]propionamide
N-[1-(p-Fluorophenyl)-4-methyl-2-pyrazolin-3-yl]formamide
N-(5-Methyl-1-phenyl-2-pyrazolin-3-yl)propionamide
N-[1-(p-Fluorophenyl)-5-phenyl-2-pyrazolin-3-yl]formamide
N-[5-(p-Chlorophenyl)-1-(m-fluorophenyl)-2-pyrazolin-3-yl]-formamide
N-[5-(p-Chlorophenyl)-1-phenyl-2-pyrazolin-3-yl]formamide
N-[1-(p-Chlorophenyl)-5-phenyl-2-pyrazolin-3-yl]formamide
N-[1,5-Bis(p-chlorophenyl)-2-pyrazolin-3-yl]formamide The compounds of the present invention have been found to be highly useful for the above pharmaceutical therapy, when administered in amounts ranging from about 0.5 milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active ingredient for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, intra-articular, topical or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquid and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are for example, myristyl-gamma-picolinium chloride, phenyl mercuric nitrate, benzalkonium chloride, phenethyl alcohol, p-chlorophenyl-α-glycerol ether, methyl and propyl parabens, and thimerosol. As a practical matter it is also convenient to employ antioxidants. Suitable antioxidants include, for example sodium bisulfite, *sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The compounds of this invention are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin, excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives a dye and flavoring such as cherry or orange flavor. Of course, any material used in preparing any dosage unit form should be pharmaceutically pure and substantially non-toxic in the amounts employed.

For the control of asthma or allergic responses, the active ingredient may also be administered by inhalation. For the inhalation routes, an inhaler device may be employed with the active ingredient in a suitable form such as powder or solution with appropriate pharmaceutical carriers.

This invention will be described in greater detail in conjunction with the following examples:

EXAMPLE 1

N-[1-(3,4-Dichlorophenyl)-2-pyrazolin-3-yl]-2,2,2-trifluoroacetamide

A 9.9 g. amount of sodium metal is dissolved in 450 ml. of absolute ethanol, then 75.0 g. of 3,4-dichlorophenylhydrazine hydrochloride is added followed in 10 minutes by 19.5 g. of acrylonitrile. The reaction mixture is refluxed for 18 hours. The solvent is removed in vacuo. Water is added to separate a granular solid. The solid is dissolved in acetone and filtered to remove a small amount of insoluble material. The filtrate is evaporated to dryness leaving a solid. The solid is triturated with ether to give 62.4 g. of 3-amino-1-(3,4-dichlorophenyl)-2-pyrazoline as a tan crystalline solid, m.p. 181°–183° C.

A 10.0 g. amount of the preceding product is added portionwise with cooling and stirring to 50 ml. of trifluoroacetic anhydride with separation of a solid. The reaction mixture is stirred for 3 hours at room temperature then the solid is collected by filtration and dried to give 12.2 g. of product. A 3.0 g. amount of this material is recrystallized from dichloromethane-hexane to give 2.4 g. of the product of the Example as pale yellow needles, m.p. 163°–164° C.

EXAMPLE 2 p-Chloro-N-[1-(3,4-dichlorophenyl)-2-pyrazolin-3-yl]benzamide

A stirred mixture of 2.30 g. of 3-amino-1-(3,4-dichlorophenyl)-2-pyrazoline (prepared as described in Example 1) in 20 ml. of dry pyridine is cooled in an ice bath, then 2.10 g. of p-chlorobenzoyl chloride is added. The reaction mixture is allowed to stand at room temperature for 16 hours then is poured into water to separate a solid. The solid is collected by filtration and dissolved in dichloromethane. This solution is passed through a short column of a hydrous magnesium silicate. The effluent is refluxed and hexane is added until turbidity results. The solution is cooled and filtered to collect a product. The product is recrystallized from the same solvent pair to give 1.8 g. of the desired product as yellow needles, m.p. 177°–178° C.

EXAMPLE 3

2,2,2-Trifluoro-N-[5-p-tolyl-1-(p-trifluoroacetylphenyl)-2-pyrazolin-3-yl]acetamide A 1.0 g. amount of sodium metal salt is dissolved in 100 ml. of absolute ethanol, then 20.0 ml. of phenylhydrazine is added followed in 5 minutes by 24.0 ml. of (mixed cis and trans) 4-methylcinnamonitrile. The reaction mixture is refluxed for 4 hours then is cooled. The precipitate is collected by filtration then is recrystallized from acetone-hexane after treatment with activated charcoal to give 14.25 g. of 3-amino-1-phenyl-5-p-tolyl-2-pyrazoline as pale orange needles, m.p. 165°–166° C.

A mixture of 5.0 g. of the preceding product and 25 ml. of trifluoroacetic anhydride is allowed to stand at room temperature for 5 minutes. The mixture is filtered and the solid collected is dissolved in dichloromethane, then the solution is evaporated to dryness. The residue is again dissolved in dichloromethane and is passed through a hydrous magnesium silicate and recrystallized as described in Example 2 to give 1.5 g. of the product of the Example as matted pale yellow needles, m.p. 206°–207° C.

EXAMPLE 4

2,2,2-Trifluoro-N-[5-phenyl-1-(p-trifluoroacetylphenyl)-2-pyrazolin-3-yl]acetamide A 2.0 g. amount of sodium metal is dissolved in 150 ml. of absolute ethanol, then 40.0 ml. of phenylhydrazine is added followed in 5 minutes by 48.0 ml. of cinnamonitrile. The reaction mixture is refluxed for 3 hours with exothermic crystallization of a product. The product is collected by filtration and washed with water. The material is recrystallized from absolute ethanol to give 56.0 g. of 3-amino-1,5-diphenyl-2-pyrazoline as a solid, m.p. 195°–197° C.

A mixture of 5.0 g. of the above product and 25.0 ml. of trifluoroacetic anhydride is allowed to stand at room temperature for 16 hours. The solvent is removed in vacuo and the residue is taken up in dichloromethane. The solution is passed through a short column of a hydrous magnesium silicate and the product is recrystallized from the effluent as described in Example 2. The entire recrystallization procedure is repeated to give 3.0 g. of the desired product as yellow needles, m.p. 197°–198° C.

EXAMPLE 5

2,2,2-Trifluoro-N-[5-methyl-1-(p-trifluoroacetylphenyl)-2-pyrazolin-3-yl]acetamide (A) A 2.0 g. amount of sodium metal is dissolved in 200 ml. of absolute ethanol, then 32.4 g. of phenylhydrazine in 50 ml. of ethanol is added, followed in 10 minutes by 20.1 g. of crotononitrile. The reaction mixture is refluxed for 5 hours. Most of the ethanol is removed in vacuo, water is added and the product is collected by filtration. The solid is dissolved in dichloromethane. This solution is passed through a short column of a hydrous magnesium silicate. The column effluent is then refluxed on a steam bath with the gradual addition of hexane to crystallize a product. The product is collected and recrystallized from acetone-hexane to give 26.9 g. of 3-amino-5-methyl-1-phenyl-2-pyrazoline as colorless prisms, m.p. 103.5°–106° C.

(B) A mixture of 5.0 g. of the preceding compound and 25.0 ml. of trifluoroacetic anhydride is allowed to stand at room temperature for 48 hours. Dichloromethane is added to dissolve the residual sludge. The solution is evaporated to dryness in vacuo. The residue is dissolved in dichloromethane. The solution is passed through a short column of a hydrous magnesium silicate. Hexane is added to the effluent to separate a green oily precipitate. The solvent is decanted and evaporated to give a solid. The solid is again dissolved in dichloromethane, column treated as above and recrystallized by the addition of hexane. The product is collected by filtration and the above procedure is repeated to give 1.15 g. of the product of the Example as yellow matted needles, m.p. 189°–190.5° C.

EXAMPLE 6

2,2,2-Trifluoro-N-(4-methyl-1-phenyl-2-pyrazolin-3-yl)acetamide

A 2.0 g. amount of sodium metal is dissolved in 200 ml. of absolute ethanol, then 37.4 g. of phenylhydrazine is added followed in 10 minutes by 20.1 g. of methacrylonitrile. The reaction mixture is refluxed for 4 hours then is evaporated to near dryness in vacuo. Water is added to the residue to separate an oil. The oil is crystallized on standing. The solid is dissolved in dichloromethane and the solution is passed through a short column of a hydrous magnesium silicate. The column effluent is evaporated to give an oil. The oil is crystallized from acetone-hexane then is recrystallized from the same solvent pair to give 20.88 g. of 3-amino-4-methyl-1-phenyl-2-pyrazoline as colorless crystals, m.p. 83°–84° C.

A mixture of 5.0 g. of the preceding compound and 25.0 ml. of trifluoroacetic anhydride is allowed to stand for 2 minutes. The solid which separates is collected by filtration and washed with hexane. The solid is dissolved in dichloromethane. This solution is passed through a hydrous magnesium silicate and recrystallized as described in Example 2 to give 1.82 g. of the desired product as needles, m.p. 142°–143.5° C.

EXAMPLE 7

2,2,2-Trifluoro-N-[4-methyl-1-(p-trifluoroacetylphenyl)-2-pyrazolin-3-yl]acetamide A mixture of 5.0 g. of 3-amino-4-methyl-1-phenyl-2-pyrazoline (prepared as described in Example 6) and 25.0 ml. of trifluoroacetic anhydride is allowed to stand at room temperature for 24 hours. Dichloromethane is added to dissolve the solid formed then the solvent is evaporated. The solid is again dissolved in dichloromethane. This solution is columnized and recrystallized as described in Example 2 to give 5.2 g. of the product of the Example as pale yellow needles, m.p. 203°–204° C.

EXAMPLE 8

2,2,2-Trifluoro-N-[1-(p-trifluoroacetylphenyl)-2-pyrazolin-3-yl]acetamide

A 2.0 g. amount of sodium metal is dissolved in 100 ml. of absolute ethanol, then 40.0 ml. of phenylhydrazine is added followed by 26.0 ml. of acrylonitrile. The reaction mixture is refluxed for 3 hours with exothermic crystallization of a product. The product is collected by filtration and washed with 95% ethanol. The material is recrystallized from dichloromethane-benzene to give 43.6 g. of 3-amino-1-phenyl-2-pyrazoline as a solid, m.p. 168°–170.5° C.

A mixture of 1.5 g. of the preceding product and 8.0 ml. of trifluoroacetic anhydride (exothermic reaction) is allowed to stand at room temperature for one hour. The mixture is evaporated to dryness in vacuo then dichloromethane is added. The solution is filtered and the filtrate is evaporated to give 1.2 g. of the desired product as yellow needles, m.p. 228.5°–230.5° C.

EXAMPLE 9

N-(1,5-Diphenyl-2-pyrazolin-3-yl)-2,2,2-trifluoroacetamide

A 5.0 g. amount of 3-amino-1,5-diphenyl-2-pyrazoline (prepared in Example 4) and 25.0 ml. of trifluoroacetic anhydride is heated until solution. After standing for 2 minutes, the precipitate formed is collected by filtration and washed with hexane. The solid is dissolved in dichloromethane and passed through a short column of a hydrous magnesium silicate. The effluent is refluxed and hexane is added to crystallize the product. The product is recrystallized from hexane to give 0.95 g. of the desired product as needles, m.p. 151.5°–153.5° C.

EXAMPLE 10

N-[1-(m-Chlorophenyl)-2-pyrazolin-3-yl]-2,2,2-trifluoroacetamide (A) A 1.0 g. amount of sodium metal is dissolved in 100 ml. of absolute ethanol, then 30.75 g. of m-chlorophenylhydrazine is added followed in 5 minutes by 12.0 g. of acrylonitrile. The reaction mixture is refluxed for 5 hours then is cooled and filtered. The solid collected is dissolved in acetone, treated with activated charcoal and filtered. Hexane is added to the filtrate to crystallize the product which is collected to give 30.7 g. of 3-amino-1-(m-chlorophenyl)-2-pyrazoline as off-white prisms, m.p. 131°–132° C.

(B) A 5.0 g. amount of the above product is added to 25.0 ml. of trifluoroacetic anhydride giving an exothermic reaction with formation of a precipitate. After 5 minutes standing, the precipitates is collected by filtration. The solid is dissolved in dichloromethane then is passed through a short column of a hydrous magnesium silicate. The effluent is refluxed and hexane is added until turbidity results. Then the mixture is cooled and filtered to provide 4.7 g. of the desired product as yellow crystals, m.p. 143°–144° C.

EXAMPLE 11

N-[1,5-Bis(p-chlorophenyl)-2-pyrazolin-3-yl]-2,2,2-trifluoroacetamide

Sodium metal (2.8 g.) is dissolved in 125 ml. of absolute ethanol, then 17.9 g. of p-chlorophenylhydrazine hydrochloride is added followed by 16.36 g. of p-chlorocinnamonitrile. The reaction mixture is refluxed for 7 hours and is allowed to stand at room temperature for 16 hours. The solvent is removed in vacuo and water is added to separate a solid. The solid is collected by filtration, dissolved in dichloromethane, and is columnized and crystallized as for Example 9. The product is recrystallized from acetone-hexane to give 10.0 g. of 3-amino-1,5-bis(p-chlorophenyl)-2-pyrazoline as colorless needles, m.p. 150°–150.5° C.

A 5.0 g. amount of the preceding compound is mixed with 25.0 ml. of trifluoroacetic anhydride at room temperature. The mixture is allowed to stand for 16 hours, then is filtered. The solid is dissolved in dichloromethane. The filtered. The solid is dissolved in dichloromethane. The give 4.52 g. of the desired product as light yellow matted needles, m.p. 138.5°–140° C.

EXAMPLE 12

2-Bromo-N-[1-($\alpha,\alpha,\alpha$-trifluoro-m-tolyl)-2-pyrazolin-3-yl]-propionamide Sodium metal (2.8 g.) is dissolved in 125 ml. of absolute ethanol, then 21.2 g. of m-trifluoromethylphenylhydrazine hydrochloride is added followed by 5.5 g. of acrylonitrile. The reaction mixture is refluxed for 18 hours. The solvent is removed in vacuo and water is added to the residue to give a tacky solid. The solid is dissolved in dichloromethane. The solution is dried over anhydrous magnesium sulfate and passed through a short column of a hydrous magnesium silicate. The effluent is collected and concentrated to separate tan crystals. This material is recrystallized from acetone-hexane to give 14.8 g. of 3-amino-1-($\alpha,\alpha,\alpha$-trifluoro-m-tolyl)-2-pyrazoline as pale yellow needles, m.p. 104°–105° C.

To 100 ml. of chloroform with stirring is added 2.75 g. of potassium carbonate and 5.3 g. of 3-amino-1-($\alpha,\alpha,\alpha$-trifluoro-m-tolyl)-2-pyrazoline, then 5.0 g. of $\alpha$-bromopropionylchloride is added dropwise. After the addition is complete the reaction mixture is refluxed on a steam bath for 4 hours. Then the solvent is removed in vacuo and water is added to give a gum. The gum is extracted with dichloromethane. The extracts are combined and dried over anhydrous magnesium sulfate. The solution is passed through a short column of a hydrous magnesium silicate, then is evaporated leaving a gummy solid. The solid is triturated with ether to give 1.13 g. of a yellow solid. The solid is recrystallized from acetone-hexane to give the desired product as yellow crystals, m.p. 54°–56° C.

EXAMPLE 13

2-Dimethylamino-N-[1-($\alpha,\alpha,\alpha$-trifluoro-m-tolyl)-2-pyrazolin-3-yl]propionamide A 1.0 g. amount of 2-bromo-N-[1-($\alpha,\alpha,\alpha$-trifluoro-m-tolyl)-2-pyrazolin-3-yl]propionamide (Example 12) is dissolved in 50 ml. of benzene in a pressure bottle, then 2.0 ml. of dimethylamine is added and the bottle is sealed for ½ hour at room temperature with the separation of crystals. The mixture is heated on a steam bath for 6 hours, then is cooled. The reaction mixture is partitioned between water and benzene. The benzene layer is dried over anhydrous magnesium sulfate and evaporated to a dark gum. The gum is dissolved in hexane and filtered through a hydrous magnesium silicate. The filtrate is evaporated to a gum (0.9 g.). A 210 mg. amount of this gum is chromatographed by thick layer chromatography on one mm Silica Gel G plates using the upper phase of a mixture of 2 parts benzene, 1 part acetone and 2 parts water to give 180 mg. of the desired product as a light yellow gum.

EXAMPLE 14

N-[1-(3,4-Dichlorophenyl)-5-methyl-2-pyrazolin-3-yl]-2,2,2-trifluoroacetamide (A) A 2.8 g. amount of sodium metal is dissolved in 125 ml. of absolute ethanol, then 21.35 g. of 3,4-dichlorophenylhydrazine hydrochloride is added followed in 5 minutes by 6.7 g. of crotononitrile. The reaction mixture is refluxed for 8 hours, then is evaporated to dryness in vacuo. Water is added to separate an oil. The oil is crystallized, then is dissolved in dichloromethane and is passed through a short column of a hydrous magnesium silicate. The effluent is refluxed with the gradual addition of hexane to separate 14.4 g. of 3-amino-1-(3,4-dichlorophenyl)-5-methyl-2-pyrazoline as colorless prisms, m.p. 103°–104° C.

(B) A mixture of 2.5 g. of the above compound and 15.0 ml. of trifluoroacetic anhydride is allowed to stand at room temperature for one hour. The reaction mixture is filtered to collect a solid. The solid is dissolved in dichloromethane. This solution is passed through a short column of a hydrous magnesium silicate. The effluent is heated on a steam bath and hexane is added to crystallize a product. The product is collected, then the entire crystallization procedure is repeated to give 2.50 g. of the product of the Example as needles, m.p. 150°–152° C.

EXAMPLE 15

N-[1-(3,4-Dichlorophenyl)-4-methyl-2-pyrazolin-3-yl]-formamide

A 2.8 g. amount of sodium metal is dissolved in 200 ml. of absolute ethanol, then 21.35 g. of 3,4-dichlorophenylhydrazine hydrochloride is added followed in 30 minutes by 6.7 g. of methacrylonitrile. The reaction mixture is refluxed for 5 hours, then is evaporated to dryness in vacuo. Water is added to separate a solid. The solid is collected and dissolved in dichloromethane. This solution is passed through a short column of a hydrous magnesium silicate and recrystallized as described in Example 2 to give 16.65 g. of 3-amino-1-(3,4-dichlorophenyl)-4-methyl-2-pyrazoline as colorless prisms, m.p. 131°–132.5° C.

A mixture of 3.0 g. of the preceding compound and 15 ml. of a mixture of formic acid and acetic anhydride (Feiser and Feiser, Reagents for Organic Synthesis, Vol. 1, page 4) is allowed to stand at room temperature for ½ hour. The reaction mixture is poured onto ice then is filtered to collect a solid. The solid is dissolved in dichloromethane and treated as described in Example 2 to give 2.72 g. of the desired product as yellow prisms, m.p. 150°–152° C.

EXAMPLE 16

N-[1-(3,4-Dichlorophenyl)-2-pyrazolin-3-yl]formamide

A mixture of 5.0 g. of 3-amino-1-(3,4-dichlorophenyl)-2-pyrazoline (prepared in Example 1) and 25 ml. of a mixture of formic acid and acetic anhydride (Example 15) is allowed to stand at room temperature for one hour. The resulting solid is collected by filtration and washed with hexane. The solid is dissolved in dichloromethane and is columnized and recrystallized as described in Example 5 to give 3.85 g. of the desired product as yellow prisms, m.p. 151°–153° C.

EXAMPLE 17

N-[1-(4-Biphenylyl)-5-methyl-2-pyrazolin-3-yl]-2,2,2-trifluoroacetamide

A 5.0 g. amount of 4-amino-biphenyl is suspended in a stirred solution of 40.0 ml. of concentrated hydrochloric acid and 27.0 ml. of water maintained at 5° C. Stirring is continued and the temperature is maintained below 10° C. during the slow addition of a solution of 8.0 g. of sodium nitrite in 16.0 ml. of water. The reaction mixture is stirred for 15 minutes longer at 5° C. then is added slowly to a cooled solution (0°–5° C.) of 53.0 g. of stannous chloride in 53.0 ml. of concentrated hydrochloric acid. The resulting mixture is diluted with water and treated with a 40% solution of sodium hydroxide until alkaline. The solid formed is collected by filtration, dissolved in dichloromethane, dried over anhydrous magnesium sulfate and filtered. The filtrate is passed through a short column of a hydrous magnesium silicate. The effluent is evaporated in vacuo to give a solid. The solid is dissolved in dichloromethane. This solution is heated to boiling and hexane is added until trubidity occurs. The mixture is cooled and filtered to give 8.5 g. of 4-biphenylhydrazine as orange crystals, m.p. 135°–138° C. (dec.).

A 4.3 g. amount of the preceding compound is added to a solution of 0.1 g. of sodium metal dissolved in 100 ml. of absolute ethanol. Then 1.54 g. of crotononitrile is added and the mixture is refluxed for 6 hours and poured into water to separate a dark solid. The solid is dissolved in dichloromethane, heated to reflux and recrystallized twice with hexane as previously described to give 3.6 g. of 3-amino-1-(4-biphenylyl)-5-methyl-2-pyrazoline as a solid, m.p. 174°–176° C.

A 0.5 g. amount of the preceding compound is dissolved in 2.5 ml. of trifluoroacetic anhydride and allowed to remain at room temperature for 2 hours. The solvent is removed in vacuo and water is added to separate a solid. The solid is collected, dissolved in dichloromethane and is columnized and recrystallized as in Example 2 to give the product of the Example as yellow crystals, m.p. 192°–193° C.

EXAMPLE 18

N-(1-Phenyl-2-pyrazolin-3-yl)acetamide

A 10.0 g. amount of 3-amino-1-phenyl-2-pyrazoline (prepared in Example 8) and 10.0 ml. of acetic anhydride are mixed together and allowed to stand at room temperature for one hour. The resulting solid is collected, dissolved in dichloromethane and passed through a short column of a hydrous magnesium silicate. The effluent is heated and hexane is added to crystallize 1.2 g. of the desired product as yellow prisms, m.p. 190°–191° C.

EXAMPLE 19

N-[1-(m-Chlorophenyl)-2-pyrazolin-3-yl]formamide

A mixture of 2.0 g. of 3-amino-1-(m-chlorophenyl)-2-pyrazoline (prepared in Example 10) and 10 ml. of a mixture of formic acid and acetic anhydride (Example 15) is allowed to stand at room temperature for 30 minutes. Then the solvent is evaporated in vacuo to give an oil. The oil is dissolved in dichloromethane and is columnized and recrystallized as described in Example 5 to give 1.32 g. of the desired product as pale yellow needles, m.p. 143°–145° C.

EXAMPLE 20

N-[1-(p-Chlorophenyl)-5-methyl-2-pyrazolin-3-yl]formamide

A 1.72 g. amount of sodium metal is dissolved in 10 ml. of absolute ethanol, then 11.0 g. of p-chlorophenylhydrazine hydrochloride is added followed in 15 minutes by 4.20 g. of crotononitrile. The reaction mixture is refluxed for 18 hours. The solvent is removed in vacuo and water is added to the residue to separate a gum. The gum is dissolved in dichloromethane and separated from the aqueous layer. The organic layer is dried over anhydrous magnesium sulfate and filtered through a short column of a hydrous magnesium silicate. The effluent is evaporated to give a glass. A small amount of benzene and then hexane is added to the glass which gradually solidifies. The solid is collected, washed with hexane and dried to give 8.1 g. of 3-amino-1-(p-chlorophenyl)-5-methyl-2-pyrazoline as a pink solid, m.p. 90°–92° C.

A 4.8 g. amount of the above compound is dissolved in 25.0 ml. of a mixture of formic acid and acetic anhydride (Example 15). The reaction mixture is allowed to remain at room temperature for 3 hours, then ice water is added to separate a gum. The aqueous phase is decanted and the gum is dissolved in dichloromethane. The solution is dried over magnesium sulfate and passed through a hydrous magnesium silicate. The effluent is evaporated leaving a gum. The gum is dissolved in dichloromethane. The solution is heated and hexane is added until turbidity results. The mixture is cooled and filtered to yield 3.6 g. of the desired product as off-white crystals, m.p. 112°–113° C.

EXAMPLE 21

N-[1-(p-Chlorophenyl)-5-methyl-2-pyrazolin-3-yl]-2,2,2-trifluoroacetamide

An 8.0 g. amount of 3-amino-1-(p-chlorophenyl)-5-methyl-2-pyrazoline (prepared as described in Example 20) is dissolved in 25.0 ml. of dichloromethane with stirring. This solution is slowly added with stirring to 25.0 ml. of trifluoroacetic anhydride cooled at 10° C. The reaction mixture is stirred for 3 hours at room temperature, then the solvent is removed in vacuo. The residue is dissolved in dichloromethane and this solution is passed through a short column of a hydrous magnesium silicate. The effluent is concentrated while adding hexane until turbidity results. The solution is cooled, then filtered to give 8.5 g. of N-[1-(p-chlorophenyl)-5-methyl-2-pyrazolin-3-yl]-2,2,2-trifluoroacetamide as a white solid, m.p. 170°–172° C.

EXAMPLE 22

N-(1-Phenyl-2-pyrazolin-3-yl)formamide

A mixture of 10.0 g. of 3-amino-1-phenyl-2-pyrozoline (prepared in Example 8) and 50.0 ml. of a mixture of formic acid and acetic anhydride (Example 15) is allowed to stand at room temperature for 3 hours. Water is added and the white crystals are collected by filtration. The solid is dissolved in dichloromethane. The solution is dried over magnesium sulfate and filtered through a hydrous magnesium silicate. The filtrate is evaporated in vacuo to give pink crystals. A 500 mg. portion of crude product is recrystallized from dichloromethane-hexane to give 403 mg. of the desired product as a white solid, m.p. 140°–141° C.

EXAMPLE 23

N-[1-(p-Chlorophenyl)-4-methyl-2-pyrazolin-3-yl]formamide

A 1.2 g. amount of sodium metal is dissolved in 110 ml. of absolute ethanol, then 7.5 g. of p-chlorophenylhydrazine hydrochloride is added followed by 2.9 g. of methacrylonitrile. The reaction mixture is refluxed for 18 hours. The solvent is removed in vacuo and water is added to the residue to separate a gum. The gum is collected and dissolved in dichloromethane. The organic solution is washed with water, dried over anhydrous magnesium sulfate and filtered through a short column of a hydrous magnesium silicate. The effluent is evaporated leaving a gum which solidifies upon adding hexane. The solid is collected and recrystallized from ether-hexane to give 4.6 g. of 3-amino-1-(p-chlorophenyl)-4-methyl-2-pyrazoline as white crystals, m.p. 107°–108° C.

A 2.2 g. amount of the preceding compound is dissolved in 10.0 ml. of a mixture of formic acid and acetic anhydride (Example 15). The mixture is allowed to remain at room temperature for 3 hours. Water is added and a yellow solid is collected by filtration. The solid is dissolved in dichloromethane. The solution is dried over anhydrous magnesium sulfate and filtered through a hydrous magnesium silicate. The filtrate is concentrated while adding hexane until turbidity occurs. The mixture is cooled and filtered to give 2.1 g. of the product of the Example as a white solid, m.p. 172°–174° C.

EXAMPLE 24

N-[1-(m-Chlorophenyl)-4-methyl-2-pyrazolin-3-yl]formamide

A 3.12 g. amount of sodium metal is dissolved in 200 ml. of absolute ethanol, then 20.9 g. of m-chlorophenylhydrazine hydrochloride is added, followed by 7.6 g. of methacrylonitrile. The reaction mixture is refluxed for 18 hours. The solvent is removed in vacuo and water is added to separate a solid. The solid is collected, dissolved in dichloromethane, dried over anhydrous magnesium sulfate and filtered through a hydrous magnesium silicate. The filtrate is evaporated to give a solid. The solid is recrystallized twice from ether-hexane to give 16.2 g. of 3-amino-1-(m-chlorophenyl)-4-methyl-2-pyrazoline as white crystals, m.p. 84°–85° C.

A 3.0 g. amount of the preceding product is dissolved in 10 ml. of a mixture of formic acid and acetic anhydride (Example 15). The mixture is allowed to remain at room temperature for 3 hours, then is poured into ice water to separate a partial gum and solid. This material is collected, dissolved in dichloromethane and filtered through a short column of a hydrous magnesium silicate. The effluent is concentrated while adding hexane to separate 3.1 g. of the product of the Example as light yellow crystals, m.p. 140°–142° C.

EXAMPLE 25

N-(5-Methyl-1-phenyl-2-pyrazolin-3-yl)acetamide

A mixture of 2.0 g. of 3-amino-5-methyl-1-phenyl-2-pyrazoline (prepared in Example 5), 5.0 ml. of acetic anhydride and 100 mg. of 4-dimethylaminopyridine is allowed to stand at room temperature for 3 hours. The mixture is filtered to give a white solid. The solid is dissolved in dichloromethane and is columnized and recrystallized as for Example 14 (B) to give 0.90 g. of the desired product as colorless plates, m.p. 144.5°–146.5° C.

EXAMPLE 26

N-[1-(p-Fluorophenyl)-5-methyl-2-pyrazolin-3-yl]acetamide (A) Sodium metal (2.8 g.) is dissolved in 200 ml. of absolute ethanol, then 16.73 g. of p-fluorophenylhyrazine hydrochloride is added followed in 10 minutes by 6.7 g. of crotononitrile. The reaction mixture is refluxed for 16 hours. The solvent is removed in vacuo and water is added to the residue to separate a solid. The solid is dissolved in dichloromethane. The solution is passed through a short column of a hydrous magnesium silicate. The effluent is refluxed and hexane is added to crystallize 11.0 g. of 3-amino-1-(p-fluorophenyl)-5-methyl-2-pyrazoline as prisms, m.p. 133°–135° C.

(B) A mixture of 3.0 g. of the preceding compound and 7.5 ml. of acetic anhydride is allowed to remain at room temperature for 16 hours. The mixture is filtered to collect a solid. The solid is dissolved in dichloromethane. The solution is columnized and crystallized as for Example 14 (B) to give 1.3 g. of the product of the Example as colorless needles, m.p. 136.5°–137.5° C.

EXAMPLE 27

N-[5-(p-Chlorophenyl)-1-(m-fluorophenyl)-2-pyrazolin-3-yl]acetamide

A 1.4 g. amount of sodium metal is dissolved in 150 ml. of absolute ethanol, then 8.1 g. of m-fluorophenylhydrazine hydrochloride is added followed in 5 minutes by 8.18 g of p-chlorocinnamonitrile. The reaction mixture is heated at reflux for 6 hours, then is filtered and cooled. The solvent is partially evaporated and water is added to separate a semi-solid which is collected, dissolved in dichloromethane and is columnized and crystallized twice as for Example 9 to give 2.4 g. of 3-amino-5-(p-chlorophenyl)-1-(m-fluorophenyl)-2-pyrazoline as colorless needles, m.p. 135.5°–136° C.

A mixture of 2.5 g. of the above compound and 7.5 ml. of acetic anhydride is allowed to stand at room temperature for 16 hours. The resulting clear dark solution is poured into a mixture of 50 ml. of water, 50 ml. of ethanol and 20 ml. of 5 N sodium hydroxide. The reaction mixture is refluxed for 30 minutes on a steam bath, then is cooled and filtered to collect a solid. The solid is dissolved in dichloromethane and is columnized and crystallized as for Example 10 (B) to give 1.82 g. of the desired product as yellow needles, m.p. 182°–183.5° C.

EXAMPLE 28

N-[5-(p-Chlorophenyl)-1-(p-fluorophenyl)-2-pyrazolin-3-yl]acetamide

A 2.8 g. amount of sodium metal is dissolved in 100 ml. of absolute ethanol, then 16.26 g. of p-fluorophenylhydrazine hydrochloride is added followed in 5 minutes by 16.35 g. of p-chlorocinnamonitrile. The reaction mixture is refluxed for 20 hours, then the solvent is evaporated in vacuo. Water is added to separate a solid. The solid is dissolved in dichloromethane and is columnized and crystallized as for Example 5 (A) to yield 8.95 g. of 3-amino-5-[p-chlorophenyl]-1-(p-fluorophenyl)-2-pyrazoline as a pale coral colored solid, m.p. 182°–183° C.

A mixture of 4.0 g. of the preceding product and 15.0 ml. of acetic anhydride is allowed to stand at room temperature for 16 hours. Then the mixture is poured into a mixture of 50 ml. of water, 50 ml. of 95% ethanol and 55 ml. of 5 N aqueous sodium hydroxide. The reaction mixture is refluxed on a steam bath for 30 minutes, then is cooled and filtered to collect a solid. The solid is dissolved in dichloromethane and is columnized and crystallized as for Example 10 (B) to yield 2.3 g. of the product of the Example as off-white needles, m.p. 133°–135° C.

EXAMPLE 29

N-[1-(p-Chlorophenyl)-2-pyrazolin-3-yl]acetamide

Sodium metal (2.8 g.) is dissolved in 200 ml. of absolute ethanol, then 17.9 g. of p-chlorophenylhydrazine hydrochloride is added followed in 25 minutes by 5.5 g. of acrylonitrile. The reaction mixture is refluxed for 6 hours, then is filtered hot. The filtrate is evaporated to dryness in vacuo, then water is added to separate a solid. The solid is collected by filtration, then is dissolved in dichloromethane and columnized and crystallized as for Example 10 (B) to give 8.75 g. of 3-amino-1-(p-chlorophenyl)-2-pyrazoline as colorless needles, m.p. 142.5°–145° C.

A mixture of 0.5 g. of the preceding product and 1.25 ml. of acetic anhydride is allowed to remain at room temperature for 16 hours. The mixture is chilled and filtered to give 222 mg. of pale yellow crystals. The material is recrystallized from dichloromethane-hexane to give the product of the Example as a white solid, m.p. 168°–170° C.

EXAMPLE 30

N-[1-(p-Chlorophenyl)-4-methyl-2-pyrazolin-3-yl]-2,2,2-trifluoroacetamide

A 7.0 g. amount of 3-amino-1-(p-chlorophenyl)-4-methyl-2-pyrazoline (prepared as described in Example 23) is dissolved in 25.0 ml. of dichloromethane and cooled to 5° C. The solution is stirred and 14.0 ml. of trifluoroacetic anhydride is added. Stirring is continued at room temperature for 3 hours, then the solvent is removed in vacuo. The residue is dissolved in dichloromethane and the solution is concentrated with the addition of hexane until turbidity appears. The mixture is cooled and the solid is collected to give 5.3 g. of product. A 1.0 g. amount of this material is recrystallized from dichloromethane-hexane to give 750 mg. of the desired product as a white solid, m.p. 181°–183° C.

EXAMPLE 31

N-[1-(p-Chlorophenyl)-4-methyl-2-pyrazolin-3-yl]acetamide

A 9.0 g. amount of 3-amino-1-(p-chlorophenyl)-4-methyl-2-pyrazoline (prepared as described in Example 23) is dissolved in 54.0 ml. of acetic anhydride. The warm solution is allowed to stand for 16 hours at room temperature with some solid separation. The solid is collected by filtration and is dissolved in methanol. Then 1 N potassium hydroxide in methanol is added to make basic. After 15 minutes at room temperature, the solvent is removed in vacuo and water is added to separate a solid. The solid is collected and recrystallized from dichloromethane-hexane to give 6.5 g. of the desired product as white crystals, m.p. 172°–173° C.

EXAMPLE 32

N-[1-(p-Chlorophenyl)-5-methyl-2-pyrazolin-3-yl]acetamide

A mixture of 8.0 g. of 3-amino-1-(p-chlorophenyl)-5-methyl-2-pyrazoline (prepared as described in Example 20), 400 mg. of 4-dimethylaminopyridine and 20.0 ml. of acetic anhydride is allowed to stand at room temperature for 48 hours. The solid formed is collected by filtration, washed with cold acetic anhydride, then with hexane and is dried to give a white solid. The solid is recrystallized from dichloromethane-hexane to give 6.6 g. of the product of the Example as a white solid, m.p. 167°–169° C.

EXAMPLE 33

N-(4-Methyl-1-phenyl-2-pyrazolin-3-yl)acetamide

A 10.0 g. amount of 3-amino-4-methyl-1-phenyl-2-pyrazoline (prepared as described in Example 6) is dissolved in 50 ml. of acetic anhydride, then 500 mg. of 4-dimethylaminopyridine is added and the reaction mixture is allowed to stand at room temperature for 18 hours. The mixture is poured into water to separate a gum which solidifies and is collected by filtration. The solid is added with stirring to 150 ml. of methanol containing 10.0 g. of sodium hydroxide. After 30 minutes, the solvent is removed in vacuo and water is added to provide a gum which becomes solid. This solid is dissolved in dichloromethane, dried over anhydrous magnesium sulfate and passed through a short column of a hydrous magnesium silicate. The effluent is concentrated while adding hexane to yield crystals. The material is collected and dried to give 3.3 g. of the desired product as a white solid, m.p. 149°–150° C.

EXAMPLE 34

N-[1-(p-Trifluoroacetylphenyl)-2-pyrazolin-3-yl]acetamide

A mixture of 800 mg. of N-(1-phenyl-2-pyrazolin-3-yl)acetamide (Example 18) and 5.0 ml. of trifluoroacetic anhydride is allowed to stand at room temperature for 30 minutes. Then the mixture is evaporated to dryness in vacuo. The residue is dissolved in dichloromethane and is columnized and crystallized as for Example 10 (B) to yield 85 mg. of the desired product as yellow needles, m.p. 243°–244° C.

EXAMPLE 35

N-(1-Phenyl-2-pyrazolin-3-yl)propionamide

A mixture of 10.0 g. of 3-amino-1-phenyl-2-pyrazoline (prepared as described in Example 8), 50 ml. of propionic anhydride and 200 mg. of 4-dimethylaminopyridine is kept at room temperature for 30 minutes. The mixture is cooled and filtered to give yellow crystals. The solid is dissolved in dichloromethane and is columnized and crystallized as for Example 10 (B) to yield 4.55 g. of the product of the Example as colorless crystals, m.p. 170.5°–171° C.

EXAMPLE 36

N-[1-(m-Fluorophenyl)-4-methyl-2-pyrazolin-3-yl]acetamide

A 2.8 g. amount of sodium metal is dissolved in 200 ml. of absolute ethanol, then 16.2 g. of m-fluorophenylhydrazine hydrochloride is added, followed by 13.4 g. of methacrylonitrile. The reaction mixture is refluxed for 18 hours, then the solvent is evaporated in vacuo. Water is added to give a gum. The gum is dissolved in dichloromethane and the solution is passed through a short column of a hydrous magnesium silicate. The effluent is concentrated while adding hexane until turbidity occurs. The solution is cooled and seeded to separate a pink solid which is collected by filtration and dried to give 4.2 g. of 3-amino-1-(m-fluorophenyl)-4-methyl-2-pyrazoline.

A 4.2 g. amount of the preceding compound is dissolved in 10.0 ml. of acetic anhydride then 100 mg. of 4-dimethylaminopyridine is added and the reaction mixture is allowed to stand at room temperature for 16 hours. The mixture is poured into water to separate a gum which solidifies. The solid is collected by filtration and washed with water. The solid is dissolved in 50.0 ml. of methanol and 10.0 ml. of 1 N sodium hydroxide in methanol is added. The mixture is allowed to stand at room temperature for 30 minutes, then the solvent is partly removed in vacuo. The addition of water separates a yellow solid. The solid is collected and dried to give 4.1 g. of the product of the Example, m.p. 171°–172° C.

EXAMPLE 37

N-(1-m-Tolyl-2-pyrazolin-3-yl)acetamide

A 2.8 g. amount of sodium metal is dissolved in 100 ml. of absolute ethanol, then 15.8 g. of m-tolylhydrazine hydrochloride is added followed in 5 minutes by 9.9 g. of β-ethoxypropionitrile. The reaction mixture is refluxed for 16 hours, then is evaporated to dryness in vacuo. Water is added to the residue to separate a solid. The solid is dissolved in dichloromethane and is columnized and crystallized as described in Example 26 (A) to give 10.1 g. of 3-amino-1-m-tolyl-2-pyrazoline as colorless crystals, m.p. 119°–120° C.

A mixture of 3.0 g. of the above compound, 15.0 ml. of acetic anhydride and 150 mg. of 4-dimethylaminopyridine is allowed to stand at room temperature for 16 hours. The mixture is filtered to collect a small amount of solid. The solid is washed with hexane. The filtrate is allowed to stand for 16 hours and is filtered to collect additional solid. This material is washed with hexane. The solids are combined and again washed with hexane to give 1.72 g. of the desired product as off-white crystals, m.p. 222°–225° C.

EXAMPLE 38

2,2,2-Trifluoro-N-(1-phenyl-2-pyrazolin-3-yl)acetamide

A mixture of 5.0 g. of 3-amino-1-phenyl-2-pyrazoline (prepared as described in Example 8), 200 ml. of dichloromethane, 5.0 ml. of triethylamine and 7.0 ml. of trifluoroacetic anhydride is allowed to remain at room temperature for 30 minutes. The mixture is evaporated to dryness in vacuo, then water is added to separate a semi-solid. The solid is dissolved in dichloromethane. The solution is dried over anhydrous sodium sulfate, columnized and recrystallized as for Example 14 (B) to give 3.0 g. of the desired product as yellow-orange prisms, m.p. 163°–165° C.

EXAMPLE 39

2,2,2-Trifluoro-N-[4-methyl-1-(α,α,α-trifluoro-m-tolyl)-2-pyrazolin-3-yl]acetamide A 0.7 g. amount of sodium metal is dissolved in 35.0 ml. of absolute ethanol, then 5.3 g. of m-trifluoromethylphenylhydrazine hydrochloride is added followed slowly by the addition of 1.7 g. of methacrylonitrile. The reaction mixture is refluxed for 18 hours. The solvent is removed in vacuo and water is added to separate a solid. The solid is collected and dissolved in dichloromethane. The solution is dried over anhydrous magnesium sulfate then is passed through a short column of a hydrous magnesium silicate. The effluent is evaporated to give a solid. The solid is recrystallized from ether-hexane to give 3.6 g. of (±)-3-amino-4-methyl-1-(α,α,α-trifluoro-m-tolyl)-2-pyrazoline as white crystals.

A 7.9 g. amount of the preceding compound (prepared as described above) is dissolved in 25.0 ml. of dichloromethane, then 15.8 ml. of trifluoroacetic anhydride is added and the mixture is stirred at room temperature for 2½ hours. The excess anhydride is removed in vacuo and the reaction is repeated using hexane as the medium. The reaction mixture is again evaporated in vacuo and the resulting tan solid is dissolved in ether and is filtered through a 200 mesh synthetic magnesium silicate adsorbent. The filtrate is concentrated while adding hexane to precipitate white crystals. The mixture is cooled for 16 hours and filtered to yield 8.4 g. of the desired product, m.p. 121°–122° C.

EXAMPLE 40

N-(1,5-Diphenyl-2-pyrazolin-3-yl)formamide

A mixture of 5.0 g. of 3-amino-1,5-diphenyl-2-pyrazoline (prepared as described in Example 4) and 25.0 ml. of a mixture of formic acid and acetic anhydride (Example 15) is allowed to remain at room temperature for 30 minutes. The hexane is added and the mixture is filtered. The solid obtained is dissolved in dichloromethane. The solution is columnized and recrystallized as described in Example 14 (B) to yield 3.55 g. of the product of the Example as off-white needles, m.p. 158°–160° C.

EXAMPLE 41

2,2,2-Trifluoro-N-[1-(p-fluorophenyl)-2-pyrazolin-3-yl]acetamide

Sodium metal (2.8 g.) is dissolved in 100 ml. of absolute ethanol, then 16.26 g. of p-fluorophenylhydrazine hydrochloride is added followed in 5 minutes by 5.5 g. of acrylonitrile. The reaction mixture is refluxed for 7 hours, then the solvent is evaporated near dryness and water is added to separate a solid. The solid is dissolved in dichloromethane. The solution is columnized and the product is recrystallized as for Example 5 (A) to give 6.6 g. of 3-amino-1-(p-fluorophenyl)-2-pyrazoline as colorless needles, m.p. 114°–115° C.

A mixture of 4.15 g. of the preceding product, 100 ml. of dichloromethane and 10.0 ml. of trifluoroacetic anhydride is allowed to remain at room temperature for 30 minutes. The mixture is evaporated to dryness in vacuo. The resulting solid is washed with water, then is dissolved in dichloromethane. The solution is columnized and the desired product is recrystallized as for Example 14 (A) to yield 5.45 g. as pale yellow prisms, m.p. 145.5°–147° C.

EXAMPLE 42

2,2,2-Trifluoro-N-[1-(4-trifluoroacetyl-m-tolyl)-2-pyrazolin-3-yl]acetamide

A mixture of 4.0 g. of 3-amino-1-m-tolyl-2-pyrazoline (prepared in Example 37) and 20.0 ml. of trifluoroacetic anhydride is stirred at room temperature giving an exothermic reaction resulting in a green solution. The solution is cooled to provide a precipitate. The solvent is evaporated in vacuo to give a solid. The solid is dissolved in dichloromethane. The solution is columnized and the desired product is recrystallized as described in Example 26 (A) to give 3.9 g. of the product of the Example as yellow needles, m.p. 171.5°–173° C.

EXAMPLE 43

2,2,2-Trifluoro-N-[1-(p-fluorophenyl)-5-phenyl-2-pyrazolin-3-yl]acetamide

Sodium metal (2.8 g.) is dissolved in 100 ml. of absolute ethanol, then 16.2 g. of p-fluorophenylhydrazine hydrochloride is added followed in 5 minutes by 12.9 g. of cinnamonitrile. The reaction mixture is refluxed for 5 hours. Then the solvent is evaporated in vacuo. Water is added to separate a solid. The solid is dissolved in dichloromethane and is columnized and recrystallized 3 times as described in Example 26 (A) to give 6.2 g. of 3-amino-1-(p-fluorophenyl)-5-phenyl-2-pyrazoline as buff colored needles, m.p. 160°–161° C.

A mixture of 4.0 g. of the preceding compound, 50 ml. of dichloromethane and 10 ml. of trifluoroacetic anhydride is allowed to remain at room temperature for 30 minutes. The solvent is evaporated in vacuo. The residual solid is washed with water and dried. The solid is dissolved in dichloromethane. The solution is columnized and the desired product is recrystallized as described in Example 26 (A) to give 4.36 g. as colorless matted needles, m.p. 143°–143.5° C.

EXAMPLE 44

2,2,2-Trifluoro-N-[1-(p-fluorophenyl)-5-methyl-2-pyrazolin-3-yl]acetamide

An 8.4 g. amount of sodium metal is dissolved in 420 ml. of absolute ethanol, then 48.8 g. of p-fluorophenylhydrazine hydrochloride is added, followed in 5 minutes by 20.1 g. of crotononitrile. The reaction mixture is refluxed for 16 hours. The solvent is removed in vacuo and water is added to separate a solid. The solid is collected by filtration and dissolved in dichloromethane. The solution is columnized and a product is recrystallized as for Example 26 (A) to give 25.5 g. of 3-amino-1-(p-fluorophenyl)-5-methyl-2-pyrazoline as prisms, m.p. 135°–136° C.

A mixture of 10.0 g. of the preceding product, 50 ml. of dichloromethane and 25 ml. of trifluoroacetic anhydride is allowed to remain at room temperature for 30 minutes. The solvent is removed in vacuo and water is added to separate a solid. The solid is collected and washed with a saturated sodium bicarbonate solution. The solid is dissolved in dichloromethane. The solution is columnized and recrystallized twice as described in Example 26 (A) to give 11.15 g. of the product of the Example as yellow crystals, m.p. 116°–117° C.

EXAMPLE 45

N-[1-(p-Fluorophenyl)-5-methyl-2-pyrazolin-3-yl]propionamide

A mixture of 3.0 g. of 3-amino-1-(p-fluorophenyl)-5-methyl-2-pyrazoline (prepared in Example 44) and 5.0 ml. of propionic anhydride is allowed to remain at room temperature for 2 hours. The reaction mixture is poured into water and the water is decanted. This step is repeated. The precipitate is treated with saturated sodium bicarbonate solution then is filtered. The solid is dissolved in dichloromethane. The solution is columnized and the desired product is recrystallized as described in Example 26 (A) to give 2.77 g. as colorless plates, m.p. 125°–126.5° C.

EXAMPLE 46

N-[1-(p-Fluorophenyl)-4-methyl-2-pyrazolin-3-yl]formamide

A 2.8 g. amount of sodium metal is dissolved in 150 ml. of absolute ethanol, then 16.26 g. of p-fluorophenylhydrazine hydrochloride is added followed in 5 minutes by 6.7 g. of methacrylonitrile. The reaction mixture is refluxed for 8 hours, then the solvent is removed in vacuo. Water is added to the residue to separate an oil. The oil crystallizes on standing for 16 hours. The solid is dissolved in dichloromethane and is columnized and recrystallized twice as described in Example 26 (A) to give 8.65 g. of 3-amino-1-(p-fluorophenyl)-4-methyl-2-pyrazoline as colorless prisms.

A mixture of 3.3 g. of the above compound and 15.0 ml. of a mixture of formic acid and acetic anhydride (Example 15) is allowed to remain at room temperature for 16 hours. Water is added and the mixture is filtered. The solid collected is recrystallized from acetone-hexane to give 2.65 g. of the desired product as pale yellow prisms, m.p. 166°–168.5° C.

EXAMPLE 47

N-(5-Methyl-1-phenyl-2-pyrazolin-3-yl)propionamide

A mixture of 5.0 g. of 3-amino-5-methyl-1-phenyl-2-pyrazoline (prepared in Example 5) and 25.0 ml. of propionic anhydride is allowed to remain at room temperature for 16 hours. The reaction mixture is poured into water to separate an oil which crystallizes. The solid is collected by filtration and dissolved in dichloromethane. The solution is passed through a short column of a hydrous magnesium silicate. The effluent is heated at reflux and hexane is added. The first heavy precipitate (purple color) is discarded. The solution is cooled and the ensuing precipitate is collected by filtration. The solid is again dissolved in dichloromethane, columnized and recrystallized with hexane to give 2.3 g. of the product of the Example as plates, m.p. 96.0°–96.5° C.

EXAMPLE 48

N-[1-(p-Fluorophenyl)-5-phenyl-2-pyrazolin-3-yl]formamide

A mixture of 5.0 g. of 3-amino-1-(p-fluorophenyl)-5-phenyl-2-pyrazoline (prepared as described in Example 43) and 85.0 ml. of a mixture of formic acid and acetic anhydride (Example 15) is allowed to remain at room temperature for 2 hours. The solvent is evaporated in vacuo to give an oil. Water is added to separate a solid. The solid is dissolved in dichloromethane and is columnized and recrystallized twice as described in Example 26 (A) to give 3.55 g. of the desired product as colorless crystals, m.p. 158.5°–160.5° C.

EXAMPLE 49

N-[5-(p-Chlorophenyl)-1-(m-fluorophenyl)-2-pyrazolin-3-yl]formamide (A) Sodium metal (1.4 g.) is dissolved in 150 ml. of absolute ethanol. The solution is cooled in a cold water bath, then 8.1 g. of m-fluorophenylhydrazine hydrochloride is added followed in 5 minutes by 8.18 g. of p-chlorocinnamonitrile. The reaction mixture is heated at reflux for 6 hours then is filtered. The filtrate is cooled and water is added. The semi-solid is collected by filtration, dissolved in dichloromethane and is columnized and recrystallized twice as described in Example 26 (A) to give 2.4 g. of 3-amino-5-(p-chlorophenyl)-1-(m-fluorophenyl)-2-pyrazoline as colorless needles, m.p. 135.5°–136° C.

(B) A mixture of 2.0 g. of the preceding compound and 10.0 ml. of a mixture of formic acid and acetic anhydride (Example 15) is allowed to remain at room temperature for 2 hours. The mixture is poured into water to separate an oil which becomes semi-solid. The material is decanted, then water is added and the solid is collected by filtration. The solid is dissolved in dichloromethane and is columnized and recrystallized as described in Example 26 (A) to yeild 1.02 g. of the desired product as off-white needles, m.p. 128.5°–130.5° C.

EXAMPLE 50

N-[5-(p-Chlorophenyl)-1-phenyl-2-pyrazolin-3-yl]formamide

A mixture of 500 ml. of absolute ethanol, 5.0 ml. of 50% choline is methanol, 32.4 g. of phenylhydrazine and 49.08 g. of p-chlorocinnamonitrile is refluxed for 7 hours, then is allowed to stand at room temperature for 16 hours. The solvent is evaporated in vacuo. The solid is dissolved in dichloromethane and the solution is columnized and recrystallized twice as described in Example 26 (A) to give 12.0 g. of 3-amino-5-(p-chlorophenyl)-1-phenyl-2-pyrazoline as colorless needles, m.p. 183.5°–185.5° C.

A mixture of 10.0 g. of the preceding product and 100 ml. of a mixture of formic acid and acetic anhydride (Example 15) is allowed to remain at room temperature for 2.5 hours. The mixture is poured into water to separate a semi-solid. The procedure of Example 49 (B) is followed to yield 6.3 g. of the desired product as yellow prisms, m.p. 135°–136° C.; resolidifies, then melts, m.p. 149°–150° C.

EXAMPLE 51

N-[1-(p-Chlorophenyl)-5-phenyl-2-pyrazolin-3-yl]formamide

A 5.52 g. amount of sodium metal is dissolved in 300 ml. of absolute methanol. The solution is cooled in a cold water bath, then 35.8 g. of p-chlorophenylhydrazine hydrochloride is added followed in 5 minutes by 25.9 g. of cinnamonitrile. After 2 hours, the mixture is cooled to give a precipitate. Water is added and the mixture is extracted with dichloromethane. The organic layer is dried, then is columnized and recrystallized as described in Example 26 (A) to give 22.5 g. of crude product. A 5.0 g. amount of this material is recrystallized as above to give 3.35 g. of 3-amino-1-(p-chlorophenyl)-5-phenyl-2-pyrazoline as colorless needles, m.p. 159°–161° C.

A mixture of 15.0 g. of the above crude product and 85.0 ml. of a mixture of formic acid and acetic anhydride (Example 15) is allowed to remain at room temperature for 2 hours. The reaction mixture is poured into water and filtered to collect the solid. The solid is washed with a solution of saturated sodium bicarbonate, then water. The material is dried, dissolved in dichloromethane, then is columnized and recrystallized as above to give 12.0 g. of the desired product as pale yellow crystals. A 5.0 g. amount of this material is recrystallized as above to give 4.70 g. of the desired product, m.p. 164°–166° C.

EXAMPLE 52

N-(1,5-Diphenyl-2-pyrazolin-3-yl)propionamide

A mixture of 10.0 g. of 3-amino-1,5-diphenyl-2-pyrazoline (prepared in Example 4), 30.0 ml. of propionic anhydride and 500 mg. of 4-dimethylaminopyridine is heated on a steam bath for 3 hours. The mixture is poured into water to separate an oil. The oil crystallizes and the solid is collected by filtration. The solid is dissolved in dichloromethane. The solution is dried over anhydrous sodium sulfate then is columnized and recrystallized twice as for Example 26 (A) to give 6.0 g. of the product of the Example as colorless plates, m.p. 148.0–148.5° C.

EXAMPLE 53

N-[1-(p-Chlorophenyl)-5-phenyl-2-pyrazolin-3-yl]-2,2,2-trifluoroacetamide

A mixture of 2.75 g. of 3-amino-1-(p-chlorophenyl)-5-phenyl-2-pyrazoline (prepared in Example 51) and 10.0 ml. of trifluoroacetic anhydride is allowed to remain at room temperature for 16 hours. The solvent is evaporated in vacuo and the residue is dissolved in dichloromethane. The solution is columnized and recrystallized as for Example 26 (A) to give 2.35 g. of the desired product as pale yellow crystals, m.p. 176°–178° C.

EXAMPLE 54

N-(1-Phenyl-5-p-tolyl-2-pyrazolin-3-yl)propionamide

A mixture of 4.5 g. of 3-amino-1-phenyl-5-p-tolyl-2-pyrazoline (prepared in Example 3), 20.0 ml. of propionic anhydride and 200 mg. of 4-dimethylaminopyridine is heated on a steam bath for 2 hours. The reaction mixture is cooled to room temperature then water is added to separate a solid. The solid is collected then is dissolved in dichloromethane. The solution is passed through a short column of a hydrous magnesium silicate. The effluent is heated to reflux and hexane is added until turbidity appears. The mixture is cooled and filtered to collect a solid. The solid is recrystallized again from 80% ethanol. This material is dissolved in 100 ml. of methanol, then 200 mg. of potassium carbonate is added and the mixture is refluxed for 15 minutes. Water is added until turbidity appears. The mixture is cooled and filtered to collect the solid. The solid is dissolved in dichloromethane. This solution is columnized and recrystallized as described above to yield 2.4 g. of the desired product as colorless needles, m.p. 123.5°–125° C.

EXAMPLE 55

N-[1,5-Bis(p-chlorophenyl)-2-pyrazolin-3-yl]formamide

A 0.86 g. amount of sodium metal is dissolved in 100 ml. of absolute ethanol, then 7.0 g. of p-chlorophenylhydrazine hydrochloride is added followed in 30 minutes by 5.5 g. of p-chlorocinnamonitrile. The reaction mixture is refluxed for 16 hours then the solvent is removed in vacuo. Water is added to separate a solid. The solid is collected and dissolved in dichloromethane. The solution is passed through a short column of a hydrous magnesium silicate. The effluent is heated and hexane is added. The first oily material coming out of solution is removed by filtration. The filtrate is cooled to give a precipitate which is collected and dissolved in acetone. The solution is treated with activated charcoal and filtered. Hexane is added to the filtrate to crystallize a product. This material is recrystallized from acetone-hexane to give 1.48 g. of 3-amino-1,5-bis(p-chlorophenyl)-2-pyrazoline as colorless needles, m.p. 149°–150° C.

A mixture of 1.85 g. of 3-amino-1,5-bis(p-chlorophenyl)-2-pyrazoline (prepared as described above) and 10.0 ml. of a mixture of formic acid and acetic anhydride (Example 15) is allowed to remain at room temperature for 2 hours, then water is added and the mixture is filtered to collect a semi-solid. The solid is dissolved in dichloromethane and the solution is columnized and recrystallized twice as for Example 26 (A) to yield 1.10 g. of the product of the Example as off-white crystals, m.p. 198°–200° C.

EXAMPLE 56

| Preparation of Compressed Tablet | |
|---|---|
| Ingredient | mg./tablet |
| Active Compound | 0.5–500 |
| Dibasic Calcium Phosphate N.F. | qs |
| Starch USP | 40 |
| Modified Starch | 10 |
| Magnesium Stearate USP | 0.1–5.0 (% w/w) |

EXAMPLE 57

| Preparation of Compressed Tablet | |
|---|---|
| Ingredient | mg./tablet |
| Active Compound | 0.5–500 |
| Dibasic Calcium Phosphate N.F. | qs |
| Starch USP | 40 |
| Modified Starch | 10 |
| *Surfactant, e.g. Sodium Lauryl Sulfate | 0.1–2.0 (% w/w) |

-continued

| Preparation of Compressed Tablet | |
|---|---|
| Ingredient | mg./tablet |
| Magnesium Stearate USP | 0.1–5.0 (% w/w) |

*Other surface active agents such as disodium sulfosuccinate and nonionic surface active agents such as Span ® and Tween ® may also be employed.

EXAMPLE 58

| Preparation of Compressed Tablet | |
|---|---|
| Ingredient | mg./tablet |
| Active Compound | 0.5–500 |
| Direct Compression Sugar Agent e.g. Emdex | qs |
| Magnesium Stearate | 0.1–3.0 (% w/w) |

EXAMPLE 59

| Preparation of Hard Shell Capsule | |
|---|---|
| Ingredient | mg./capsule |
| Active Compound | 0.5–500 |
| Lactose, Spray Dried | qs |
| Magnesium Stearate | 0.1–3.0 (% w/w) |

EXAMPLE 60

| Preparation of Oral Liquid (Syrup) | |
|---|---|
| Ingredient | % w/v |
| Active Compound | 0.05–5 |
| Liquid Sugar | 75.0 |
| Methyl Paraben USP | 0.18 |
| Propyl Paraben USP | 0.02 |
| Suspending Agent e.g. Avicel | 0.5–1.0 |
| Flavoring Agent | qs |
| Purified Water qs ad | 100.0 |

EXAMPLE 61

| Preparation of Oral Liquid (Elixir) | |
|---|---|
| Ingredient | % w/v |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 62

| Preparation of Oral Suspension (Syrup) | |
|---|---|
| Ingredient | % w/v |
| Active Compound | 0.05–5 |
| Polysorbate 80 USP | 0.1 |
| Magnesium Aluminum Silicate, Colloidal | 0.3 |
| Dye | 0.001–0.5 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 63

| Preparation of Injectable Solution | |
|---|---|
| Ingredient | % w/v |
| Active Compound | 0.05–5 |
| Benzyl Alcohol N.F. | 0.9 |
| Water for Injection | 100.0 |

EXAMPLE 64

| Preparation of Injectable Oil | |
|---|---|
| Ingredient | % w/v |
| Active Compound | 0.05–5 |
| Benzyl Alcohol | 1.5 |
| Sesame Oil qs ad | 100.0 |

EXAMPLE 65

| Preparation of Intra-articular Product | |
|---|---|
| Ingredient | Amount |
| Active Compound | 2–20 mg. |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 66

| Preparation of Injectable Depo Suspension | |
|---|---|
| Ingredient | % w/v |
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

EXAMPLE 67

| Preparation of Topical Cream | |
|---|---|
| Ingredient | % w/w |
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 68

| Preparation of Topical Ointment | |
|---|---|
| Ingredient | % w/w |
| Active Compound | 0.05–5 |
| Cholesterol | 3 |
| Stearyl Alcohol | 3 |
| White Wax | 8 |
| Petrolatum, White USP qs | 100 |

We claim:

1. A method of meliorating inflammation in a mammal which comprises administering to said mammal an effective anti-inflammatory amount of a compound selected from those of the formula:

$$\begin{array}{c} R_1 \overbrace{\phantom{XX}}^{4\phantom{X}3} \text{NH} - R_4 \\ R_2 \underbrace{\phantom{XX}}_{5\phantom{X}1\phantom{X}2} N \\ | \\ R_3 \end{array}$$

wherein $R_1$ is hydrogen or lower alkyl ($C_1$–$C_4$); $R_2$ is hydrogen, lower alkyl ($C_1$–$C_4$), phenyl or $$\underset{\phantom{X}}{\bigcirc}\!\!-R_5$$

where $R_5$ is halogen; $R_3$ is $$\underset{R_7}{\overset{R_6}{\bigcirc}}\!\!-$$

where $R_6$ and $R_7$ are the same or different and may be hydrogen, chloro, fluoro, lower alkyl ($C_1$–$C_4$), trifluoromethyl or $COCF_3$; $R_4$ is —CHO or —COCF$_3$ with the proviso that when $R_4$ is —CHO then $R_2$ is phenyl or $$\underset{\phantom{X}}{\bigcirc}\!\!-R_5$$

where $R_5$ is halogen; or a nontoxic pharmaceutically acceptable salt thereof.

2. A method of meliorating inflammation or the progressive joint deterioration characteristic of arthritic disease in a mammal which comprises administering to said mammal an effective anti-inflammatory amount of a compound selected from those of the formula:

$$\begin{array}{c} R_1 \overbrace{\phantom{XX}}^{4\phantom{X}3} \text{NH} - R_4 \\ R_2 \underbrace{\phantom{XX}}_{5\phantom{X}1\phantom{X}2} N \\ | \\ R_3 \end{array}$$

wherein $R_1$ is hydrogen or lower alkyl ($C_1$–$C_4$); $R_2$ is hydrogen, lower alkyl ($C_1$–$C_4$), phenyl or

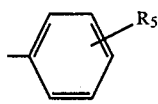

where R₅ is halogen; R₃ is

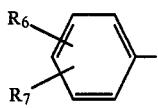

where R₆ and R₇ are the same or different and may be hydrogen, chloro, fluoro, lower alkyl (C₁-C₄), trifluoromethyl or COCF₃; R₄ is —CHO or —COCF₃ with the proviso that when R₄ is —CHO then R₂ is phenyl or

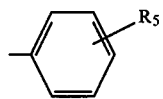

where R₅ is halogen; or a nontoxic pharmaceutically acceptable salt thereof.

3. A method of treating pain in a mammal which comprises administering to said mammal an effective analgetic amount of a compound selected from those of the formula:

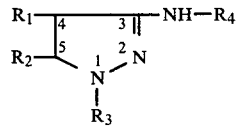

wherein R₁ is hydrogen or lower alkyl (C₁-C₄); R₂ is hydrogen, lower alkyl (C₁-C₄), phenyl or

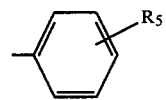

where R₅ is halogen; R₃ is

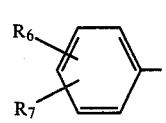

where R₆ and R₇ are the same or different and may be hydrogen, chloro, fluoro, lower alkyl (C₁-C₄), trifluoromethyl or COCF₃; R₄ is —CHO or —COCF₃ with the proviso that when R₄ is —CHO then R₂ is phenyl or

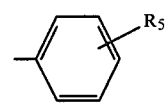

where R₅ is halogen; or a nontoxic pharmaceutically acceptable salt thereof.

4. A method of treating bacteria and/or fungal infections in a mammal which comprises administering to said mammal an effective antibacterial and/or antifungal amount of a compound selected from those of the formula:

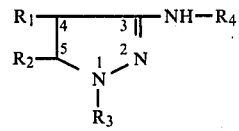

wherein R₁ is hydrogen or lower alkyl (C₁-C₄); R₂ is hydrogen, lower alkyl (C₁-C₄), phenyl or

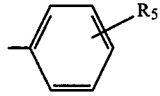

where R₅ is halogen; R₃ is

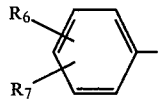

where R₆ and R₇ are the same or different and may be hydrogen, chloro, fluoro, lower alkyl (C₁-C₄), trifluoromethyl or COCF₃; R₄ is —CHO, —COCF₃ or —COR₈ where R₈ is lower alkyl (C₁-C₄) or a nontoxic pharmaceutically acceptable salt thereof.

5. A method of preventing the onset of asthmatic symptoms or allergic diseases in a mammal which comprises administering to said mammal an effective prophylactic amount for the prevention of asthmatic symptoms or allergic diseases of a compound selected from those of the formula:

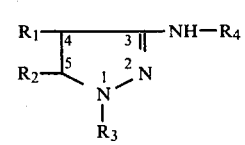

wherein R₁ is hydrogen or lower alkyl (C₁-C₄); R₂ is hydrogen, lower alkyl (C₁-C₄), phenyl or

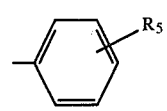

where R₅ is halogen; R₃ is

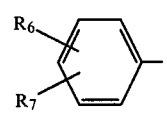

where R₆ and R₇ are the same or different and may be hydrogen, chloro, fluoro, lower alkyl (C₁-C₄), trifluoromethyl or COCF₃; R₄ is —CHO or —COCF₃ with the proviso that when R₄ is —CHO then R₂ is phenyl or

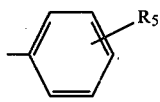

where R₅ is halogen; or a nontoxic pharmaceutically acceptable salt thereof.

6. The method according to claim 1, wherein the compound is 2,2,2-trifluoro-N-(4-methyl-1-phenyl-2-pyrazolin-3-yl)acetamide.

7. The method according to claim 1, wherein the compound is 2,2,2-trifluoro-N-(1-phenyl-2-pyrazolin-3-yl)acetamide.

8. The method according to claim 1, wherein the compound is 2,2,2-trifluoro-N-[1-(p-fluorophenyl)-2-pyrazolin-3-yl]acetamide.

9. The method according to claim 1, wherein the compound is 2,2,2-trifluoro-N-[1-(p-fluorophenyl)-5-methyl-2-pyrazolin-3-yl]acetamide.

10. The method according to claim 2, wherein the compound is 2,2,2-trifluoro-N-(4-methyl-1-phenyl-2-pyrazolin-3-yl)acetamide.

11. The method according to claim 2, wherein the compound is 2,2,2-trifluoro-N-(1-phenyl-2-pyrazolin-3-yl)acetamide.

12. The method according to claim 2, wherein the compound is 2,2,2-trifluoro-N-[1-(p-fluorophenyl)-2-pyrazolin-3-yl]acetamide.

13. The method according to claim 2, wherein the compound is 2,2,2-trifluoro-N-[1-(p-fluorophenyl)-5-methyl-2-pyrazolin-3-yl]acetamide.

14. The method according to claim 3, wherein the compound is N-[1-(3,4-dichlorophenyl)-2-pyrazolin-3-yl]-2,2,2-trifluoroacetamide.

15. The method according to claim 3, wherein the compound is 2,2,2-trifluoro-N-[5-methyl-1-(p-trifluoroacetylphenyl)-2-pyrazolin-3-yl]acetamide.

16. The method according to claim 3, wherein the compound is 2,2,2-trifluoro-N-(4-methyl-1-phenyl-2-pyrazolin-3-yl)acetamide.

17. The method according to claim 3, wherein the compound is N-(1,5-diphenyl-2-pyrazolin-3-yl)-2,2,2-trifluoroacetamide.

18. The method according to claim 3, wherein the compound is N-[1,5-bis(p-chlorophenyl)-2-pyrazolin-3-yl]-2,2,2-trifluoroacetamide.

19. The method according to claim 3, wherein the compound is N-[1-(3,4-dichlorophenyl)-5-methyl-2-pyrazolin-3-yl]-2,2,2-trifluoroacetamide.

20. The method according to claim 3, wherein the compound is 2,2,2-trifluoro-N-[4-methyl-1-(α,α,α-trifluoro-m-tolyl)-2-pyrazolin-3-yl]acetamide.

21. The method according to claim 3, wherein the compound is 2,2,2-trifluoro-N-[1-(p-fluorophenyl)-5-phenyl-2-pyrazolin-3-yl]acetamide.

22. The method according to claim 3, wherein the compound is 2,2,2-trifluoro-N-[1-(p-fluorophenyl)-5-methyl-2-pyrazolin-3-yl]acetamide.

23. The method according to claim 3, wherein the compound is N-[5-(p-chlorophenyl)-1-(m-fluorophenyl)-2-pyrazolin-3-yl]formamide.

24. The method according to claim 3, wherein the compound is N-[1,5-bis(p-chlorophenyl)-2pyrazolin-3-yl]formamide.

25. The method according to claim 4, wherein the compound is N-[1-(3,4-dichlorophenyl)-2-pyrazolin-3-yl]-2,2,2-trifluoroacetamide.

26. The method according to claim 4, wherein the compound is 2,2,2-trifluoro-N-[5-methyl-1-(p-trifluoroacetylphenyl)-2-pyrazolin-3-yl]acetamide.

27. The method according to claim 4, wherein the compound is 2,2,2-trifluoro-N-(4-methyl-1-phenyl-2-pyrazolin-3-yl)acetamide.

28. The method according to claim 4, wherein the compound is 2,2,2-trifluoro-N-[4-methyl-1-(p-trifluoroacetylphenyl)-2-pyrazolin-3-yl]acetamide.

29. The method according to claim 4, wherein the compound is N-(1,5-diphenyl-2-pyrazolin-3-yl)-2,2,2-trifluoroacetamide.

30. The method according to claim 4, wherein the compound is N-[1-(m-chlorophenyl)-2-pyrazolin-3-yl]-2,2,2-trifluoroacetamide.

31. The method according to claim 4, wherein the compound is N-[1,5-bis(p-chlorophenyl)-2-pyrazolin-3-yl]-2,2,2-trifluoroacetamide.

32. The method according to claim 4, wherein the compound is N-[1-(3,4-dichlorophenyl)-5-methyl-2-pyrazolin-3-yl]-2,2,2-trifluoroacetamide.

33. The method according to claim 4, wherein the compound is N-[1-(3,4-dichlorophenyl)-4-methyl-2-pyrazolin-3-yl]formamide.

34. The method according to claim 4, wherein the compound is N-[1-(3,4-dichlorophenyl)-2-pyrazolin-3-yl]formamide.

35. The method according to claim 4, wherein the compound is N-[1-(m-chlorophenyl)-2-pyrazolin-3-yl]formamide.

36. The method according to claim 4, wherein the compound is N-[1-(p-chlorophenyl)-5-methyl-2-pyrazolin-3-yl]formamide.

37. The method according to claim 4, wherein the compound is N-[1-(p-chlorophenyl)-5-methyl-2-pyrazolin-3-yl]-2,2,2-trifluoroacetamide.

38. The method according to claim 4, wherein the compound is N-(1-phenyl-2-pyrazolin-3-yl)formamide.

39. The method according to claim 4, wherein the compound is N-[1-m-chlorophenyl)-4-methyl-2-pyrazolin-3-yl]formamide.

40. The method according to claim 4, wherein the compound is 2,2,2-trifluoro-N-(1-phenyl-2-pyrazolin-3-yl)acetamide.

41. The method according to claim 4, wherein the compound is 2,2,2,-trifluoro-N-[4-methyl-1-(α,α,α-trifluoro-m-tolyl)-2-pyrazolin-3-yl]acetamide.

42. The method according to claim 4, wherein the compound is N-(1,5-diphenyl-2-pyrazolin-3-yl)formamide.

43. The method according to claim 4, wherein the compound is 2,2,2-trifluoro-N-[1-(p-fluorophenyl)-2-pyrazolin-3-yl]acetamide.

44. The method according to claim 4, wherein the compound is 2,2,2-trifluoro-N-[1-(4-trifluoroacetyl-m-tolyl)-2-pyrazolin-3-yl]acetamide.

45. The method according to claim 4, wherein the compound is 2,2,2-trifluoro-N-[1-(p-fluorophenyl)-5-phenyl-2-pyrazolin-3-yl]acetamide.

46. The method according to claim 4, wherein the compound is 2,2,2-trifluoro-N-[1-(p-fluorophenyl)-5-methyl-2-pyrazolin-3-yl]acetamide.

47. The method according to claim 4, wherein the compound is N-[1-(p-fluorophenyl)-4-methyl-2-pyrazolin-3-yl]formamide.

48. The method according to claim 4, wherein the compound is N-[1-(p-fluorophenyl)-5-phenyl-2-pyrazolin-3-yl]-formamide.

49. The method according to claim 4, wherein the compound is N-[5-(p-chlorophenyl)-1-(m-fluorophenyl)-2-pyrazolin-3-yl]formamide.

50. The method according to claim 4, wherein the compound is N-[5-(p-chlorophenyl)-1-phenyl-2-pyrazolin-3-yl]-formamide.

51. The method according to claim 4, wherein the compound is N-[1-(p-chlorophenyl)-5-phenyl-2-pyrazolin-3-yl]-formamide.

52. The method according to claim 4, wherein the compound is N-[1,5-bis(p-chlorophenyl)-2-pyrazolin-3-yl]-formamide.

* * * * *